United States Patent
Ueno et al.

(10) Patent No.: US 7,074,536 B2
(45) Date of Patent: Jul. 11, 2006

(54) ALKYLENEBISNAPHTOL DERIVATIVE AND CHARGE CONTROL AGENT WHICH CONSISTS OF THE SAME

(75) Inventors: Ryuzo Ueno, Nishinomiya (JP); Masaya Kitayama, Takarazuka (JP); Kenji Minami, Sennan (JP); Hiroyuki Wakamori, Hikami-gun (JP); Nobuhiro Yonetani, Nishinomiya (JP)

(73) Assignee: Kabushiki Kaisha Ueno Seiyaku Oyo Kenkyujo, Osaka (JP)

( * ) Notice: Subject to any disclaimer, the term of this patent is extended or adjusted under 35 U.S.C. 154(b) by 0 days.

(21) Appl. No.: 10/485,461

(22) PCT Filed: Jul. 30, 2002

(86) PCT No.: PCT/JP02/07700

§ 371 (c)(1),
(2), (4) Date: Jul. 12, 2004

(87) PCT Pub. No.: WO03/014058

PCT Pub. Date: Feb. 20, 2003

(65) Prior Publication Data

US 2004/0248026 A1  Dec. 9, 2004

(30) Foreign Application Priority Data

Aug. 3, 2001 (JP) ............... 2001-236303

(51) Int. Cl.
*G03G 9/097* (2006.01)

(52) U.S. Cl. .............. 430/108.2; 430/108.4; 430/108.21; 546/285; 546/329; 548/577; 562/434

(58) Field of Classification Search ........... 430/108.2, 430/108.4, 108.21; 546/285, 329; 548/577; 562/434
See application file for complete search history.

(56) References Cited

U.S. PATENT DOCUMENTS 5,200,288 A * 4/1993 Ando et al. .............. 430/108.3
5,385,799 A    1/1995 Ono et al.

FOREIGN PATENT DOCUMENTS

| EP | 490370 A1 | 6/1992 |
| EP | 548772 A1 | 6/1993 |
| EP | 0 778 501 A1 | 6/1997 |
| WO | WO 00/50512 A1 | 8/2000 |

OTHER PUBLICATIONS

European Search Report dated Aug. 23, 2005.

* cited by examiner

*Primary Examiner*—Mark A. Chapman
(74) *Attorney, Agent, or Firm*—Sughrue Mion, PLLC

(57) ABSTRACT

The present invention provides an alkylenebisnaphthol derivative represented by formula [I]:

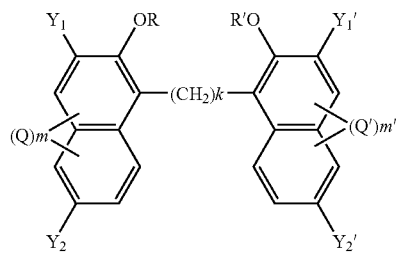

and a salt thereof. The compound of the present invention has an excellent triboelectric charge property and useful as charge control agent for electrophotographic toners.

6 Claims, 1 Drawing Sheet

ALKYLENEBISNAPHTOL DERIVATIVE AND CHARGE CONTROL AGENT WHICH CONSISTS OF THE SAME

TECHNICAL FIELD

The present invention relates to a novel alkylenebisnaphthol derivative and a charge control agent consists of the same.

BACKGROUND ART

Developers used in electrophotographic systems such as copying machine include two-component developer, which comprises carrier and toner, and single component developer, which contains no carrier. Conventional toners used in both developers are fine particles of binder resin in which colorants, such as pigment and dye, are dispersed.

One of the important properties of the toners is triboelectric chargeability. Properties required for toners include that they can generate a suitable amount of positive or negative electrostatic charge upon contacting with the carrier or charge providing device, and the amount of the charge is stable during continuous use or under an adverse environment. Binder resin, the main component of the toner may be triboelectrically chargeable but the amount of the generated electrostatic charge is not sufficient. When an image is developed with a toner containing no charge control agent, image fogging may occur to make the resulting image unclear. In order to impart further triboelectric charging property, toners in general are added with a charge control agent so that the electrostatic charge is controlled suitably.

Generally known and used charge control agent for electrophotographic toners include positively charging agents such as nigrosin dye and quaternary ammonium salt, and negatively charging agents such as metal containing monoazo dyes, metal-salicylic acid complex and copper phthalocyanine pigment.

Problems to be Solved by the Invention

Although known charge control agent, especially negative charge control agent has an excellent chargeability, they are not suitable for manufacturing color toner because of their color attributable to their main component, pigments or dyes.

Metal complex charge control agent has poor dispersibility and compatibility with the resin and may cause inhomogeneous charge of the resulting toner. Further, the agent may easily be released from the toner particles to stain on the development sleeve or carriers or lower the chargeability over continuous copying. Said problems may cause reduction of resulting image density.

Further, the complex structure of a metal containing compound like metal complex invites high manufacturing cost. The metals like chrome may affect negatively on human body and environment. There has been a demand for development of metal free charge control agent.

Japanese Patent Laid Open No. H05-11505 discloses to use a compound obtainable by linking 3-carboxy substituted 2-naphthols with alkylene such as pamo acid as a charge control agent.

The alkylenebisnaphthol derivative disclosed in this prior art has some triboelectric charging ability but the chargeable amount is low. Therefore, said derivatives cannot be used as a charge control agent for actual electrophotographic system.

In order to dissolve the above problems, an object of the present invention is to provide a novel alkylenebisnaphthol derivative which is suitably used as charge control agent for electrophotographic toner and the like.

Further object of the present invention is to provide a novel charge control agent having an excellent dispersibility and compatibility with binder resins and is suitable for manufacturing color toners, and is safe for human body as well as environment.

Still further object of the present invention is to provide electrophotographic toner of which particles can be charged uniformly within a short time period and the triboelectric charging property is stable over time. Said toner can provide high quality images with high image density and less fogging.

Solution of the Problem

The inventors have successfully synthesized novel alkylenebisnaphthol derivatives, studied their physical properties and found that the derivatives have an excellent triboelectric charging property and are useful as charge control agent for electrophotographic toners.

Accordingly, the present invention provides an alkylenebisnaphthol derivative represented by the formula [I]:

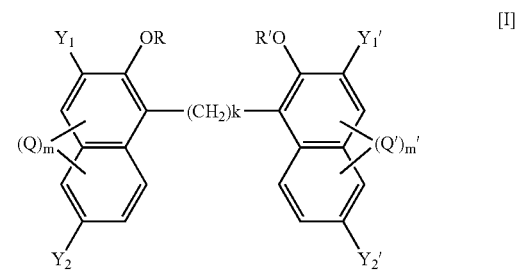

wherein $Y_1$, $Y_2$, $Y_1'$ and $Y_2'$ may be same or different and each of them is selected from the group consisting of carboxyl group, an esterified carboxyl group, a group of —(CONH)n-X (wherein X is an optionally branched and optionally substituted hydrocarbon group which may have an unsaturated bond, an optionally substituted aromatic group and a heterocyclic group having conjugated double bonds, n is an integer of 1 or 2);

k is an integer of 1–12;

R and R' are selected from the group consisting of hydrogen atom, an alkaline metal, an optionally branched and optionally substituted alkyl or acyl group of 1–6 carbon atoms and a phenylalkyl group;

Q and Q' are selected from the group consisting of an optionally branched alkyl or alkoxy group of 1–6 carbon atoms, a halogen atom, nitro group, nitroso group, amino group and sulfo group; and m and m' each represents an integer of 0–3 or a salt thereof.

The present invention further provides charge control agent consists of the above alkylenebisnaphthol derivative or its salt, and an electrophotographic toner comprising said compound as a charge control agent. Further more, the present invention provides use of the above-identified alkylenebisnaphthol derivative or a salt thereof as a charge control agent.

In the above formula, examples of esterified carboxylic groups for $Y_1$, $Y_2$, $Y_1$ and $Y_2'$ include an alkoxycarbonyl of 1–6 carbon atoms, such as methoxycarbonyl, ethoxycarbonyl, propyloxycarbonyl, isopropyloxycarbonyl, butoxycarbonyl, pentyloxycarbonyl and hexyloxycarbonyl; phenoxycarbonyl and phenacyloxycarbonyl. In case the group has an aromatic moiety, said moiety may have a substituent.

The group X may be an optionally branched and optionally substituted hydrocarbon group which may have an unsaturated bond, preferably an alkyl of 1–20 carbon atoms such as methyl, ethyl, propyl, butyl, pentyl, hexyl, decyl, dodecyl, lauryl and stearyl; an alkenyl of 2–6 carbon atoms such as vinyl, allyl, propylenyl, butylenyl, pentylenyl and hexylenyl; an optionally substituted aromatic group such as, phenyl, naphthyl, anthryl, anthraquinonyl and pyrenyl; and an optionally substituted heterocyclic group having conjugated double bonds such as benzimidazolonyl, carbazolyl, pyridyl, thiazolyl, benzothiazolyl, imidazolyl, indryl, thiofuryl, phenothiazinyl, acridinyl and quinolinyl.

Examples of substituents in each definition, wherein the group is optionally substituted, may include a halogen atom, a halogenated lower alkyl, nitro, a lower alkyl, a lower alkoxy such as methoxy, cyano, phenyl, naphthyl, phenoxy, furyl, amino, toluidylamino, triazylamino, pyrimidylamino, benzoylamino, sulfo, hydroxy, an esterified carboxyl group such as alkoxycarbonyl and phenoxycarbonyl, amidized carboxyl groups such as phenylaminocarbonyl, alkylaminosulfonyl group and an alkenyl group of 2–6 carbon atoms which may include aryl group.

When the substituent contains an aromatic ring, the compound may further have one or more substituents such as a halogen atom, a lower alkyl, a lower alkoxy, phenyl, and cyano groups on said aromatic ring.

BEST MODE FOR CARRYING OUT THE INVENTION

Figure 1:
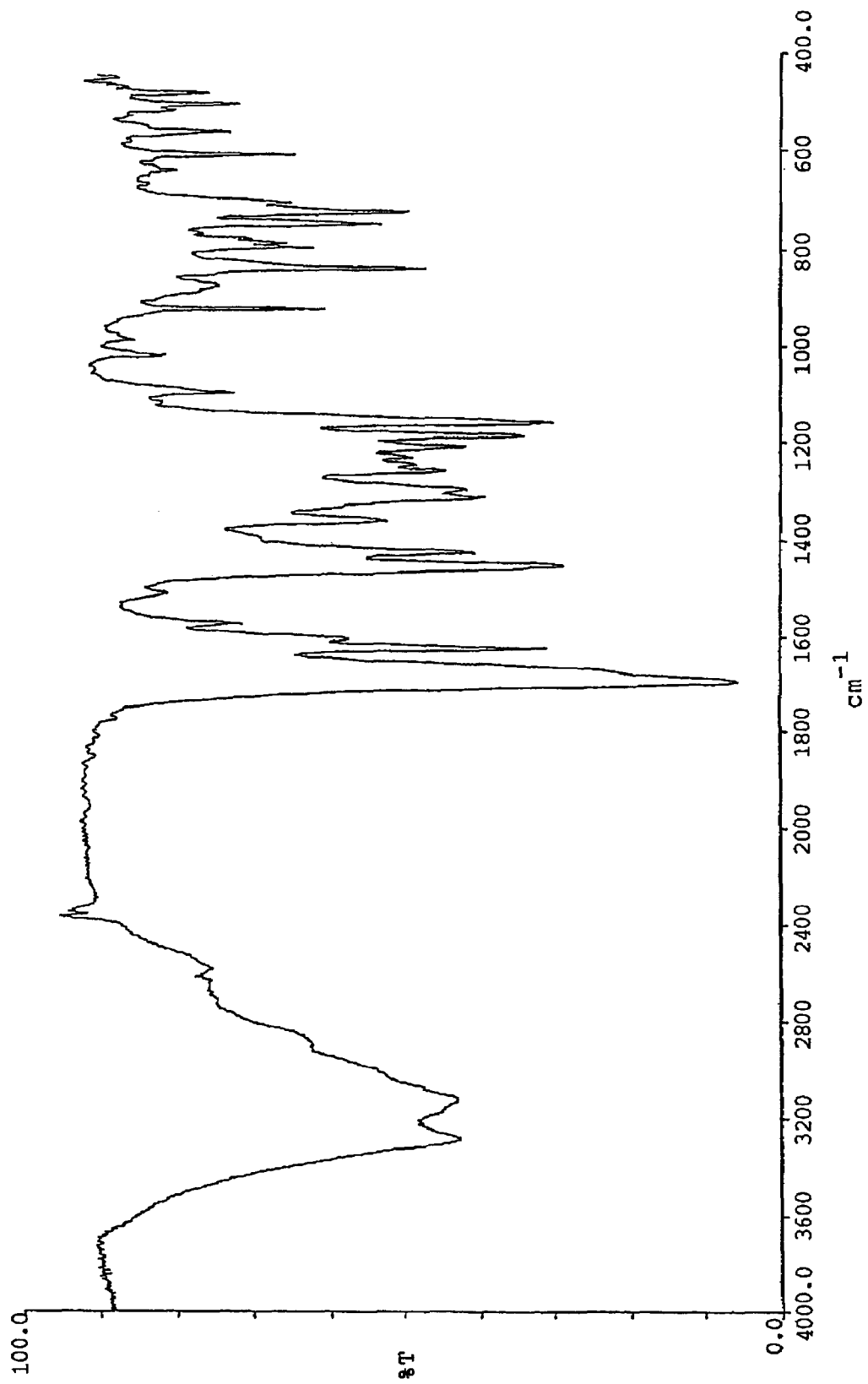
FIG. 1 is an infrared absorption spectrum (KBr) of the methylenebisnaphthol derivative obtained in Example 1.

In the present specification and claims, "lower" represents a group having 1–6 carbon atoms.

"Aromatic group" represents a 6-membered monocyclic aromatic group or condensed ring group consisting of up to 4 of 6-membered aromatic rings.

"Heterocyclic group having conjugated double bonds" represents a 5- or 6-membered mono-cyclic group or condensed ring group having at least one hetero-atom selected from N, S and O and conjugated double bonds. When it represents a condensed ring group, said group may have up to 6 rings.

In the present invention, each of the two naphthalene nuclei of the alkylenebisnaphthol derivative represented by formula [1] may have a substituent of Q or Q' respectively. Each of Q and Q' may independently be selected from the group consisting of an optionally branched alkyl or alkoxy group of 1–6 carbon atoms, halogen atom, nitro, nitroso, amino and sulfo groups.

Each of m and m', which represents the number of the substituent, is usually 0 and may be up to 3.

The number "k" represents number of carbon atoms of the alkylene moiety bridging the two naphthalene nuclei at 1 and 1' positions and is an integer of 1–12. Examples of the alkylene moiety may include methylene, ethylene, propylene, butylene, hexamethylene, octamethylene and dodecylmethylene. Among the alkylenes, methylene and ethylene are preferable, and methylene or the compound wherein k=1 is especially preferable in terms of chargeability.

R and R' are selected from the group consisting of hydrogen atom, an alkaline metal, optionally branched and optionally substituted alkyl and acyl groups of 1–6 carbon atoms and a phenylalkyl group.

According to the present invention, the salt of alkylenebisnaphthol derivative represented by formula [I] is not specifically limited and may preferably be alkaline metal salt such as sodium or potassium salt.

The alkylenebisnaphthol derivative of the present invention is negatively chargeable. The absolute value of the charge measured by the blow-off method under the condition specified below is high, i.e. equal to or more than 1.3 μC/g, preferably, 1.4–100 μC/g.

Examples of preferred alkylenebisnaphthol derivative of the present invention may include following compounds: (1)

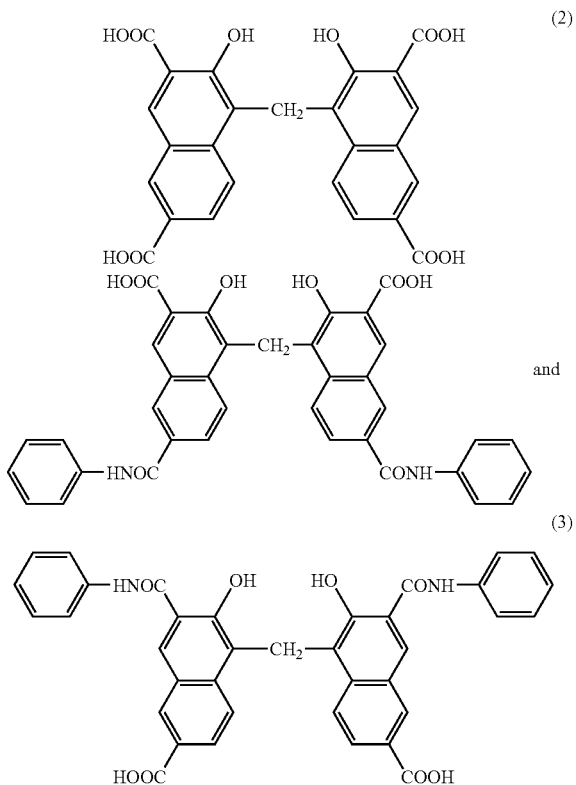

Among the above, compound (1) is most preferable due to its excellent triboelectric charging property and is suitably used as a charge control agent.

The alkylenebisnaphthol derivative of the present invention may be prepared according to the following method. The derivative of formula [I] wherein the alkylene moiety is methylene or k is 1 can be prepared by dissolving a naphthol derivative in aqueous sodium hydroxide, adding formalin to the solution and heating the mixture to 50–100° C., preferably to 90–100° C. to condense the naphthol derivative and formalin.

When the alkylene moiety is the one other than methylene, or k is 2–12, the alkylenebisnaphthol derivative of the invention may be prepared according to the following scheme:

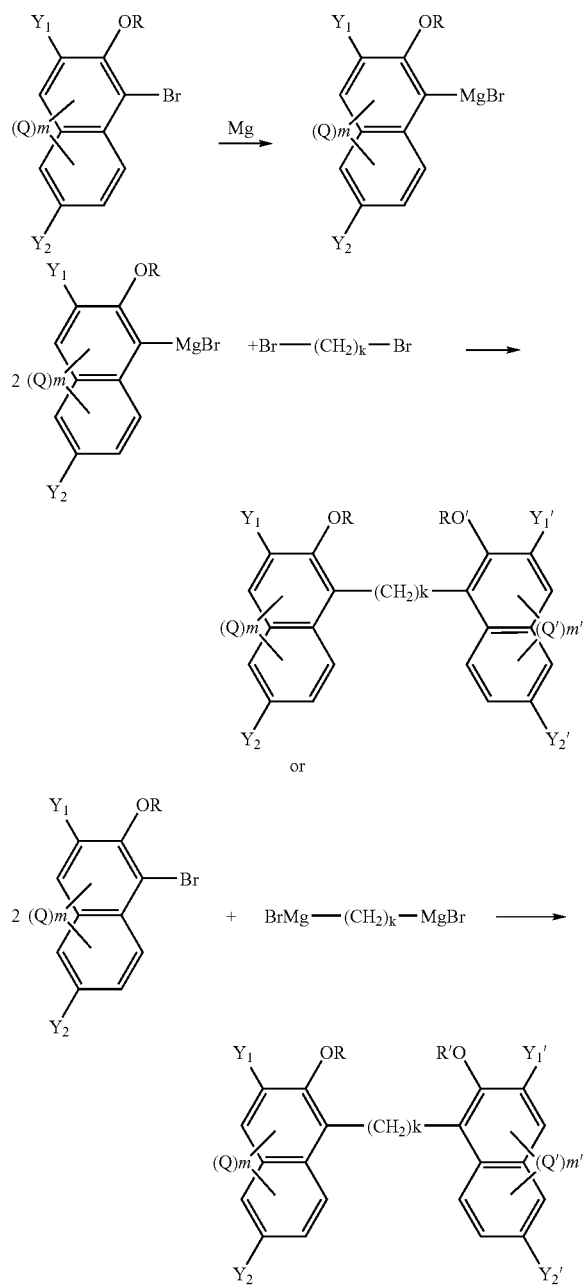

Naphthol derivatives used as starting material for preparing the alkylenebisnaphthol derivative of the invention may be prepared by the following method.

Firstly, 2-hydroxynaphthalene-3,6-dicarboxylic acid may be obtained by the method described in WO98/17621 (Japanese Patent Application No. H10-519205). That is, by reacting potassium 2-naphtholate and carbon dioxide, aciding out the reaction mixture to obtain the compound and, if desired, purifying the obtained compound.

Then, an acid chloride of thus obtained 2-hydroxynaphthalene-3,6-dicarboxylic acid may be prepared by reacting the acid with thionyl chloride or the like in a solvent such as xylene or sulfolane in a conventional manner. The amide compound is then obtained by treating the acid chloride with amine. Alternatively, 2-hydroxynaphthalene-3,6-dicarboxylic acid may be reacted directly with an amine in the presence of phosphorus trichloride or dicyclohexylcarbodiimide to give the amide compound.

An esterified naphthol derivative may be obtained by a conventional method, such as by heating 2-hydroxynaphthalene-3,6-dicarboxylic acid in an alcohol in the presence of an acid catalyst.

Further, a naphthalene derivative wherein one of the substituents at 3- and 6-positions is ester and the other is amide may be obtained from 2-hydroxynaphthalene-3,6-dicarboxylic acid by means of the method described in WO96/32366. That is, the naphthol derivative, 2-hydroxynaphthalene-3,6-dicarboxylic acid 3- or 6-mono ester and an aniline compound are reacted to effect the condensation reaction and after that, the reaction mixture may be added with water, neutralized and filtrated to give the desired compound.

Further, 1-halogenated naphthalene compound may be obtained by the following method.

2-hydroxy-3,6-dicarboxylic acid, obtainable as above, is dissolved in chloroform and dimethylsulfoxide and the mixture is cooled on ice. Halogen solution in chloroform is added dropwise thereto over 2 hours at less than 50° C. The obtained mixture is stirred for one hour and then, the solution is poured into a large amount of water. The precipitation is collected by filtration and washed with water, dispersed in methanol, concentrated under reduced pressure at room temperature and dried to give the desired 1-halogenated naphthol derivative.

The alkylenebisnaphthol derivative of the present invention has a high chargeability, high compatibility with resins, and therefore, can be dispersed uniformly in the resin. In addition, the compound has only slight color or is almost colorless, and therefore, the compound will not interfere with the color of the colorant.

Further, the alkylenebisnaphthol derivative of the present invention can be synthesized by a simple process and therefore, with low cost. No metal is contained and therefore, the derivative is safe for human being and environment. Accordingly, the novel compound of the present invention can preferably be used as a charge control agent, especially negatively chargeable charge control agent for electrophotographic toners. By using the compound of the present invention, electrophotographic toners with excellent properties can be provided.

Electrophotographic toners comprising the alkylenebisnaphthol derivative of the present invention as a charge control agent are described below. In general, toners for electrophotography are prepared by dispersing additives such as colorant and charge control agent in the binder resin. The toner of the present invention may be manufactured in a manner similar to the conventional toners using the above described alkylenebisnaphthol derivative as a charge control agent.

In manufacturing toner of the present invention, binder resins may be any of those used for conventional electrophotographic toners, for example, polystyrenes, polyacrylenes, styrene-acrylic copolymers, styrene-methacrylate copolymers, styrene-propylene copolymers, styrene-butadiene copolymers, styrene-maleic acid copolymers, olefin resins, polyesters, epoxy resins polyurethanes and polyvinyl butyrals. Those resins may be used alone or two or more of them may be used in combination.

Any of the colorants used for manufacturing conventional electrophotographic toners may preferably be used for the toner of the present invention. Examples of said colorants include carbon black, lamp black, iron black, cobalt blue, nigrosin dye, aniline blue, phthalocyanine blue, phthalocyanine green, hansa yellow, chrome yellow, rose bengal, triaryl methane dyes and monoazo and bisazo dyes or pigments. The colorants may be selected based on the desired color of the resulting toner.

The amount of the colorant per 100 parts by weight of the binder resin may preferably be 1–20 parts and preferably 2–10 parts by weight.

The toner of the present invention comprises alkylenebisnaphthol derivative of formula [I] as a charge control agent. In order to obtain toners with sufficient chargeability and good quality, the amount of the alkylenebisnaphthol derivative of formula [I] per 100 parts by weight of the binder resin may be 0.1–10, and more preferably, 0.1–5 parts by weight.

The electrophotographic toner of the present invention may comprise other known charge control agents such as metal containing monoazo dyes, metal-salicylic acid complexes and copper phthalocyanine pigments in combination with the alkylenebisnaphthol derivative of the present invention.

The toner of the present invention may further comprise additives used for manufacturing conventional toners, for example, mold-releasing agent, external additives and the like. Low molecular weight olefin polymer may preferably be used as mold-releasing agent. The external additives are those added to improve flow property, cleaning property and shelf stability of the toner. Examples of the external additives may include inorganic fine particles such as silica, alumina and titanium oxide.

The particle size of the toner is not particularly limited and preferably, equal to or less than 20 μm, more preferably, equal to or less than 10 μm.

The electrophotographic toner of the present invention may be manufactured by any known method. For example, but not limited to, the method wherein the above described ingredients are mixed uniformly by means of dry blender, Henschel mixer, ball mill or the like; the obtained mixture is melt and kneaded by means of a kneading machine such as Banbury mixer, roll extruder and single- or twin-axis extruder kneader; the uniformly kneaded matter is cooled and pulverized; and if desired, classified, and then added with the external additives to give the toner may be employed. Alternatively, any of known methods such as polymerizing method, microcapsule polymerizing method and spray dry method may be employed for the manufacture.

The charge control agent of the present invention exhibits good compatibility with resins and therefore, the agent can be admixed into the binder resin together with the other ingredients to give uniformly and stably chargeable toners. The charge control agent of the present invention may be fixed or embedded on the surface or the area adjacent to the surface of the fine particles comprising binder resin and a colorant by means of a known method using mechanical impact.

The electrophotographic toner of the present invention comprising the alkylenebisnaphthol derivative of the present invention as a charge control agent can be uniformly charged within a short time period and the triboelectric charging property is stable over time. Accordingly, by using the toner of the invention, high quality images with high image density and less fogging can be provided. Further, stain of the development sleeves and carriers with the charge control agent is effectively reduced and therefore, the toner can provide high density images stably over continuous copying.

Further more, the alkylenebisnaphthol derivative of the present invention has least impact on the resulting color and therefore, useful for manufacturing color toners.

EXAMPLES

The present invention is further described in reference to the following examples. The following examples are intended to illustrate the invention and are not to be construed to limit the scope of the invention.

Example 1

1,1-methylenebis(2-hydroxynaphthalene-3,6-dicarboxylic acid)

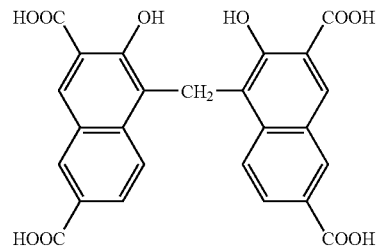

2-hydroxynaphthalene-3,6-dicarboxylic acid 9.3 g was dissolved in 10% aqueous sodium hydroxide 40 g and the solution was heated to 90° C. 37% Aqueous formalin 4.2 g was added thereto and the mixture was reacted for 2 hours at 95° C. After that, the reaction mixture was treated with carbon at 50° C. and adjusted to pH 3 with 10% aqueous hydrochloride. The precipitates were collected by filtration, washed well with water and methanol, and dried to give pale yellow powder 7.3 g (decomposition point: 294.3° C.). The infrared absorption spectrum (KBr) of the compound is shown in FIG. 1.

The triboelectric charging property of thus obtained 1,1'-methylenebis(2-hydroxynaphthalene-3,6-dicarboxylic acid) was determined by means of blow-off powder electrostatic charge tester (#TB200, Toshiba Chemical Corp, Tokyo, Japan) using metal mesh of 200-mesh (75 μm) under the condition shown below. The resulting triboelectric charge was −7.89 μC/g.

Measurement Conditions:

Temperature: 20° C.

Relative Humidity: 20%

Blow gas: $N_2$, 1.0 Kg/cm$^2$

Blow-off time: 60 seconds

Examples 2–4

Methylenebisnaphthol derivatives were synthesized in the similar manner as example 1 except for using the materials shown in table 1 below instead of 2-hydroxynaphthalene-3,6-dicarboxylic acid. The triboelectric charging property and decomposition point of thus obtained compound were determined.

TABLE 1

| Ex No | material | methylenebisnaphthol derivatives | triboelectric charge μC/g | decomposition point ° C. |
|---|---|---|---|---|
| 2 | 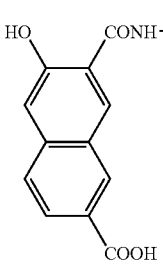 | 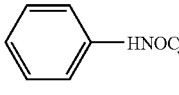 | −1.45 | 315.1 |
| 3 | 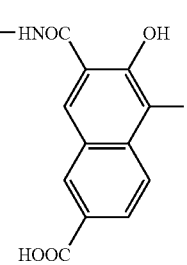 | 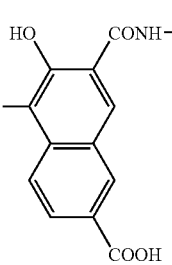 | −1.53 | 322.8 |
| 4 | 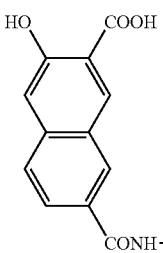 |  | −1.38 | 306.4 |

Examples 5–7

Methylenebisnaphthol derivatives are synthesized in the same manner as example 1 except for using the materials shown in table 2 below instead of 2-hydroxynaphthalene-3,6-dicarboxylic acid. The decomposition point of thus obtained compound was determined.

TABLE 2

| Ex No | material | Methylenebisnaphthol derivatives | decomposition point ° C. |
|---|---|---|---|
| 5 | 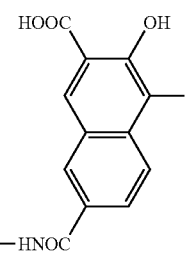 | 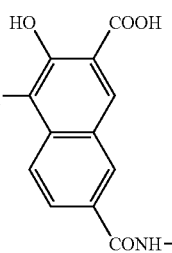 | 347.6 |

TABLE 2-continued

| Ex No | material | Methylenebisnaphthol derivatives | decomposition point ° C. |
|---|---|---|---|
| 6 | [structure: 3-hydroxy-2,6-di(n-butoxycarbonyl)naphthalene with HO, COO-n-C$_4$H$_9$, COO-n-C$_4$H$_9$] | [structure: methylenebis derivative with n-C$_4$H$_9$-OOC, OH, n-C$_4$H$_9$-OOC substituents bridged by -CH$_2$- to HO, COO-n-C$_4$H$_9$, COO-n-C$_4$H$_9$] | 300.2 |
| 7 | [structure: naphthalene with HO, CONH-(o-tolyl), CONH-(o-tolyl) substituents] | [structure: methylenebis derivative with HNOC-(o-tolyl), OH, HNOC-(o-tolyl) substituents bridged by -CH$_2$- to HO, CONH-(o-tolyl), CONH-(o-tolyl)] | 339.8 |

Comparative Examples 1–3

Methylenebisnaphthol derivatives were synthesized in the same manner as example 1 except for using the materials shown in table 3 below instead of 2-hydroxynaphthalene-3,6-dicarboxylic acid. The triboelectric charging property and decomposition point of thus obtained compound were determined.

TABLE 3

| Comp Ex | material | methylenebisnaphthol derivative | triboelectric charge μC/g | decomposition point ° C. |
|---|---|---|---|---|
| 1 | [structure: HO, COOH-substituted naphthalene] | [structure: methylenebis(hydroxynaphthalene dicarboxylic acid) with -CH$_2$- bridge] | −1.19 | 312.9 |
| 2 | [structure: 6-hydroxy-2-naphthoic acid, HO and COOH] | [structure: methylenebis(hydroxynaphthoic acid) with -CH$_2$- bridge, OH and COOH groups] | −0.76 | 325.0 |

TABLE 3-continued

| Comp Ex | material | methylenebisnaphthol derivative | tribo-electric charge μC/g | decomposition point ° C. |
|---|---|---|---|---|
| 3 | | 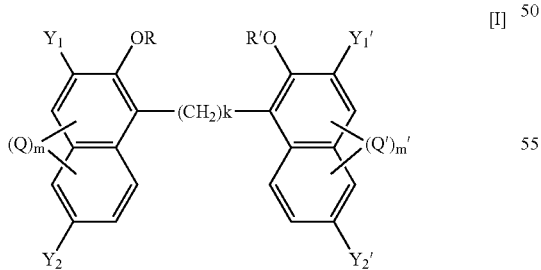 | −0.17 | 234.0 |

Examples of toners are shown below. In the following compositions, "part(s)" means "part(s) by weight".

Black Toner

Styrene-acrylic resin 100 parts, carbon black 6 parts and the compound of Example 1 2 parts are preliminary mixed uniformly with the ball mill, and then, the mixture is molten and kneaded with the dispersion kneader. The kneaded mixture is roughly crushed with the vibration mill and further pulverized with the jet mill to give the black toner.

Color Toner (Cyan)

Color toner (cyan) may be prepared in a manner similar to the black toner except for using polyester resin instead of styrene-acrylic resin and phthalocyanine blue instead of carbon black.

Color Toner (Yellow)

Color toner (yellow) may be prepared in a manner similar to the black toner except for using polyester resin instead of styrene-acrylic resin and hansa yellow instead of carbon black.

Color Toner (Magenta)

Color toner (magenta) may be prepared in a manner similar to the black toner except for using polyester resin instead of styrene-acrylic resin and rose bengal instead of carbon black.

The invention claimed is:

1. An alkylenebisnaphthol derivative represented by formula [I]:

[I]

wherein $Y_1$, $Y_2$, $Y_1'$ and $Y_2'$ may be same or different and each of them is selected from the group consisting of a carboxyl group, an esterified carboxyl group, a group of —(CONH)n-X (wherein X is an optionally branched and optionally substituted hydrocarbon group which may have an unsaturated bond, an optionally substituted aromatic group and a heterocyclic group having conjugated double bonds, n is an integer of 1 or 2);

k is an integer of 1–12;

R and R' are selected from the group consisting of hydrogen atom, an alkaline metal, an optionally branched and optionally substituted alkyl or acyl group of 1–6 carbon atoms and a phenylalkyl group;

Q and Q' are selected from the group consisting of an optionally branched alkyl or alkoxy group of 1–6 carbon atoms, a halogen atom, nitro group, nitroso group, amino group and sulfo group; and m and m' each represents an integer of 0–3 or a salt thereof.

2. The alkylenebisnaphthol derivative or a salt thereof of claim 1, wherein k is 1.

3. The alkylenebisnaphthol derivative or a salt thereof of claim 1, wherein said derivative is negatively chargeable and the absolute value of the triboelectric charge is equal to or greater than 1.3 μC/g.

4. A charge control agent consisting of an alkylenebisnaphthol derivative represented by formula [I]:

[I]

wherein $Y_1$, $Y_2$, $Y_1'$ and $Y_2'$ may be same or different and each of them is selected from the group consisting of a carboxyl group, an esterified carboxyl group, a group of —(CONH)n-X (wherein X is an optionally branched and optionally substituted hydrocarbon group which may have an unsaturated bond, an optionally substituted aromatic group and a heterocyclic group having conjugated double bonds, n is an integer of 1 or 2);

k is an integer of 1–12;

R and R' are selected from the group consisting of hydrogen atom, an alkaline metal, an optionally branched and optionally substituted alkyl or acyl group of 1–6 carbon atoms and a phenylalkyl group;

Q and Q' are selected from the group consisting of an optionally branched alkyl or alkoxy group of 1–6 carbon atoms, a halogen atom, nitro group, nitroso group, amino group and sulfo group; and m and m' each represents an integer of 0–3 or a salt thereof;

provided that said derivative is negatively chargeable and the absolute value of the triboelectric charge is equal to or greater than 1.3 μC/g.

5. A method of using an alkylenebisnaphthol derivative, comprising providing an alkylenebisnaphthol derivative as defined in claim 1 or a salt thereof as a charge control agent, provided that said derivative is negatively chargeable and the absolute value of the triboelectric charge is equal to or greater than 1.3 μC/g.

6. An electrophotographic toner, comprising at least a binder resin, a colorant and an alkylenebisnaphthol derivative of formula [I]:

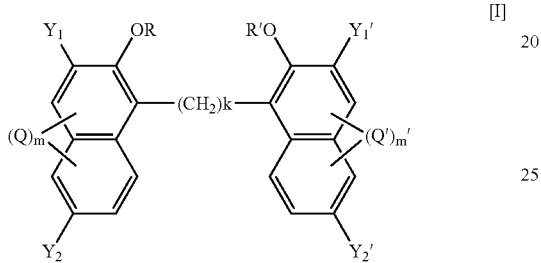

wherein $Y_1$, $Y_2$, $Y_1'$ and $Y_2'$ may be same or different and each of them is selected from the group consisting of a carboxyl group, an esterified carboxyl group, a group of —(CONH)n-X (wherein X is an optionally branched and optionally substituted hydrocarbon group which may have an unsaturated bond, an optionally substituted aromatic group and a heterocyclic group having conjugated double bonds, n is an integer of 1 or 2);

k is an integer of 1–12;

R and R' are selected from the group consisting of hydrogen atom, an alkaline metal, an optionally branched and optionally substituted alkyl or acyl group of 1–6 carbon atoms and a phenylalkyl group;

Q and Q' are selected from the group consisting of an optionally branched alkyl or alkoxy group of 1–6 carbon atoms, a halogen atom, nitro group, nitroso group, amino group and sulfo group; and m and m' each represents an integer of 0–3 or a salt thereof;

provided that said derivative is negatively chargeable and the absolute value of the triboelectric charge is equal to or greater than 1.3 μC/g.

* * * * *